United States Patent [19]

Jarcho

[11] 4,374,124
[45] Feb. 15, 1983

[54] DENTAL PLAQUE-PREVENTIVE OXAZOLIDINE CONTAINING COMPOSITIONS AND METHOD

[75] Inventor: Michael Jarcho, El Cajon, Calif.

[73] Assignee: Sterling Drug Inc., New York, N.Y.

[21] Appl. No.: 360,573

[22] Filed: Mar. 22, 1982

[51] Int. Cl.³ .......................... A61K 7/16; A61K 7/22
[52] U.S. Cl. ......................................... 424/54; 424/49
[58] Field of Search ........................................ 424/54

[56] References Cited

U.S. PATENT DOCUMENTS

| | | | |
|---|---|---|---|
| 2,964,530 | 12/1960 | Zenitz | 260/307 |
| 3,083,143 | 3/1963 | Schmid et al. | 167/93 |
| 3,120,469 | 2/1964 | Tamas | 167/93 |

*Primary Examiner*—Shep K. Rose
*Attorney, Agent, or Firm*—William G. Webb; B. Woodrow Wyatt

[57] ABSTRACT

Dental plaque-preventive compositions containing, as the active component thereof, certain 3-alkyl-4-hydroxymethyl-4-methyloxazolidines, and the method of use of the same.

6 Claims, No Drawings

DENTAL PLAQUE-PREVENTIVE OXAZOLIDINE CONTAINING COMPOSITIONS AND METHOD

BACKGROUND OF THE INVENTION

1. Field of the Invention

This invention relates to oral compositions containing certain 3-alkyl-4-hydroxymethyl-4-methyloxazolidines for preventing the formation of dental plaque and to a method of using the same for the said purpose.

2. The Prior Art

3-Hexadecyl-4-hydroxymethyl-4-methyloxazolidine and 3-octadecyl-4-hydroxymethyl-4-methyloxazolidine are disclosed and claimed in Zenitz U.S. Pat. No. 2,964,530. These compounds and their congeners are there disclosed to have anti-bacterial activity against, for example, Staphylococcus aureus, Escherichia coli, Pseudomonas aeruginosa and Asperigillus niger, and thus to be useful as anti-bacterial agents.

U.S. Pat. No. 3,083,143 discloses an anti-caries composition containing various hydroxyalkylamines.

U.S. Pat. No. 3,120,469 discloses anti-calculus compositions containing alkanolamine titanates.

SUMMARY OF THE INVENTION

In a composition aspect, this invention relates to oral hygiene compositions for the prevention of dental plaque comprising an effective amount of certain 3-alkyl-4-hydroxymethyl-4-methyloxazolidines and a compatible, pharmaceutically acceptable carrier.

In a method aspect, the invention relates to a method for treating teeth for preventing the formation of dental plaque thereon which comprises contacting the teeth with an effective amount of a 3-alkyl-4-hydroxymethyl-4-methyloxazolidine.

DETAILED DESCRIPTION INCLUSIVE OF THE PREFERRED EMBODIMENTS

More specifically, this invention provides useful compositions for the prevention of dental plaque formation containing, as the active component therein, an effective amount of a 3-alkyl-4-hydroxymethyl-4-methyloxazolidine having the formula:

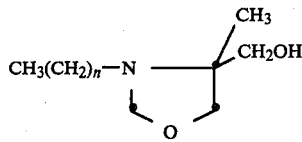

where n is an integer from 15 to 17. The preparation of the above-indicated species where n is, inter alia, 15 or 17, is fully described in Examples 4 (b) and 5 (b) of U.S. Pat. No. 2,964,530.

Dental plaque is believed to consist mainly of a mat of dextranous material which is deposited on tooth surfaces and which consists mainly of dextran having entrapped therein bacterial organisms and calcium salts. This mat, when built up on the tooth surfaces, protects the plaque-producing organisms, as well as the acid environment produced within the plaque by those organisms, from being dispersed or neutralized by the natural actions of eating and drinking. The tooth enamel and, in turn, the dentin are eroded and destroyed in the acid environment.

Efforts to eliminate or reduce the occurrence of dental caries caused by plaque formation have taken many directions. These attempts include: the use of vaccines to eliminate plaque producing organisms from the oral cavity; the complete elimination of sucrose, the substrate needed for production of dextran, from the diet; daily brushing, flossing and scraping of tooth surfaces; the modification of tooth surfaces to produce resistance to the action of the acid environment that develops as a result of bacterial metabolism; the use of "solvents" to dissolve the dextran; the use of enzyme preparations intended to either break down food particles in the mouth or to break down the dextran coating; the application of chemical substances to tooth surfaces; and the use of anti-bacterial preparations intended to interfere with the bacterial organisms which are responsible for the production of the dextran producing enzymes.

In using the anti-bacterial approach to the problem, however, it is not enough that the anti-plaque composition contain an anti-bacterial agent as the effective ingredient. Otherwise, countless numbers of compounds, having anti-bacterial activity, would be expected to be effective anti-plaque agents. On the contrary, the anti-bacterial agent, in order to be effective as an anti-plaque agent, must also have tooth substantivity, a property which permits "binding" of the anti-bacterial agent to the tooth surface in order to prevent the plaque-forming organism from colonizing the tooth surface. This, in turn, prevents the development of plaque. The 3-alkyl-4-hydroxymethyl-4-methyloxazolidines of the present anti-plaque compositions are effective for that purpose not only because they possess anti-bacterial activity against the plaque-producing organisms but because, in addition, they surprisingly also possess the essential tooth substantivity.

BIOLOGICAL TEST PRODCEDURES/RESULTS

The dental plaque preventive activity of the compounds of the present invention was determined by measuring the ability of these compounds to inhibit the production of dental plaque by Streptococcus mutans OMZ-61 as follows:

A culture medium for the plaque-producing Streptococcus mutans OMZ-61 containing 1.5 g. BBL beef extract, 5 g. of sodium chloride, 10 g. of dehydrated trypticase, 5 g. of sucrose and sufficient distilled water to give a total volume of 1,000 ml. is adjusted to pH 7.0 and sterilized by membrane filtration. The medium is dispensed aseptically in 10 ml. aliquots into 150×16 mm. test tubes and stored at refrigeration temperature until used. Two concentrations of the compound to be treated are prepared by dissolving 100 mg. of the compound in 1 ml. of distilled water (with the aid of sufficient 10% dimethylsulfoxide when needed because of low solubility) and diluting the resulting solution to 10 ml. with distilled water. This 1.0% solution and a 1:10 dilution in distilled water (0.1%) are sterilized by membrane filtration before use.

A sterile piece of plaque-free synthetic hydroxylapatite is suspended in each concentration of compound for two 1-minute periods, each followed by a 1-minute air drying period. Each piece is then suspended and agitated for 5 minutes in individual test tubes containing sterile distilled water (rinse). They are then suspended in 10 ml. of liquid beef extract medium to which has been added 0.3 ml. of a 24-hour anaerobic culture of Streptococcus mutans. The tubes containing the "treated" hydroxylapatite and the Streptococcus mutans are then incubated anaerobically at 37° C. for 24 hours. The same process of two 1-minute soaks in the solution of compound, each followed by 1 minute of air drying and the final 5 minute rinse, is repeated before once again suspending the hydroxylapatite in a fresh tube containing 10 ml. of beef extract medium and 0.3 ml. of inoculum. At the end of the second 24-hour period, each piece of hydroxylapatite is rinsed for 1 minute in three successive tubes of distilled water. These are then suspended for 1 minute in a solution of F, D and C Red NO. 3 dye. This staining procedure is used in order to identify more easily the development of plaque after the 48-hour period of exposure to the plaque-producing organism. The staining period is followed by another 10-second rinse to remove excess dye. Any plaque formation is stained a brilliant pink. Test results are read as plaque inhibition (active) or no plaque inhibition (inactive) at the percent concentration tested. An active compound is tested at successively lower doses in order to determine the minumum effective concentration. On some occasions, the interference of plaque production is caused by the inhibition of growth of the organism in the culture medium, because the compound has been leached from the hydroxylapatite surface to produce an antibacterial level in the medium. When this occurs, the compound is tested at lower concentrations until the growth of the organism in the medium surrounding the treated hydroxylaptite is equal to that in the non-medicated control culture. Plaque may or may not be formed at these lower concentrations. A compound is considered active as an anti-plaque agent when it inhibits the development of plaque on tooth surfaces but does not interfere with the growth of the plaque-producing organism in the surrounding medium.

Anti-bacterial activity of the test compounds was determined usng the standard Autotiter ® method described by Goss et al., Applied Microbiology, 16 (No. 9), 1414-16 (1968).

Data so-obtained are given in TABLE A, where concentrations of the compounds of the invention (Compound I, n is 15 or 17) are given in terms of percent by weight in the test solution and where growth or no growth, respectively, of either the test organism (S. mutans) or of the formation or non-formation of plaque are indicated by plus (+) or minus (−) signs. For comparative purposes, data are also presented for control solutions, either inoculated (Pos. Control) or uninoculated (Neg. Control) with the test organism, S. mutans. Data are also given for the comparative species, 3-n-tetradecyl-4-hydroxymethyl-4-methyloxazolidine (Ref.), which is a lower homolog (n is 13) of the compounds of the invention.

TABLE A

| Test Cpd. | % Drug | 24 Hours Growth | 48 Hours Growth | 48 Hours Plaque |
|---|---|---|---|---|
| Neg. Control | — | — | — | — |
| Pos. Control | — | + | + | ++ |
| I (n is 15) | 1.0 | + | — | — |
| I (n is 15) | 0.1 | + | + | —* |
| I (n is 15) | 0.01 | + | + | — |
| I (n is 15) | 0.005 | + | + | — |
| I (n is 15) | 0.001 | + | + | — |
| I (n is 17) | 1.0 | + | + | —* |
| I (n is 17) | 0.1 | + | + | —* |
| Ref. (n is 13) | 1.0 | + | + | ++ |
| Ref. (n is 13) | 0.1 | + | + | ++ |

*Slight pink coloration developed.

These data show that the compound of the invention where n is 15 is active at concentrations from 0.1% to 0.001% in preventing plaque formation, while not inhibiting growth of the organism S. mutans at those concentrations. The compound of the invention where n is 17 is shown to be active at concentrations from 1.0% to 0.1%. By contrast, the lower homolog, 3-n-tetradecyl-4-hydroxymethyl-4-methyloxazolidine (Ref. species), is inactive at concentrations from 1.0% to 0.1%.

In order to determine the long term effect of the tooth substantially of one of the compounds of the invention, the same procedure described above was carried out over a 4 day period using 3-n-hexadecyl-4-hydroxymethyl-4-methyloxazolidine as the test species. In this test, the same procedure followed at the end of 48 hours of the test as described above was repeated for each of the next two 24 hour periods. That is at the end of 72 hours and 96 hours total test times, the growth of the micro-organism, S. mutans, was observed and noted, and at the end of 96 hours, plaque formation was determined as before. The results obtained are given in TABLE B below:

TABLE B

| Test Cpd. | % Drug | Growth 24 Hrs. | Growth 48 Hrs. | Growth 72 Hrs. | Growth 96 Hrs. | Plaque 96 Hrs. |
|---|---|---|---|---|---|---|
| Neg. Control | — | — | — | — | — | — |
| Pos. Control | — | + | + | + | + | ++++ |
| I (n is 15) | 0.01 | + | + | + | + | — |

These results show that 3-n-hexadecyl-4-hydroxymethyl-4-methyloxazolidine, at a concentration of 0.01%, is active in preventing plaque formation for a period up to 4 days without interfering with the growth of S. mutans, thus demonstrating prolonged and effective tooth substantivity.

Finally, for purposes of determining the effective anti-plaque concentration range for 3-n-hexadecyl-4-hydroxymethyl-4-methyloxazolidine, the minimum inhibitory concentrations (MIC's) against the species S. mutans OMZ-61 and Actinomyces viscosus T-6, two of the organisms chiefly involved in dental plaque formation, were determined using standard serial dilution techniques. The MIC's so-found were 7.8 micrograms/ml. against S. mutans OMZ-61 and 15.6 micrograms/ml. against A. viscosus T-6.

The anti-plaque compounds of the invention can be formulated for use in tooth pastes, tooth powders, tooth ointments, mouth washes, troches, lozenges, chewing gums, foods, drinks etc. so as to constitute from 1.0% to 0.001% by weight of the composition.

The compounds of the invention can also be formulated for anti-plaque use by combination with other agents conventionally used in anti-plaque compositions, such as dextranase, sodium hexametaphosphate (Calgon ®) and surfactants.

I claim:

1. An oral composition for the prevention of dental plaque comprising an effective amount consisting from 1.0% to 0.001% by weight of a compound having the formula:

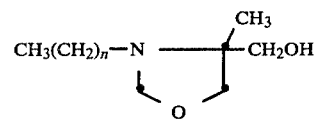

where n is an integer from 15 to 17, and a compatible, pharmaceutically acceptable tooth paste, tooth powder, tooth ointment, mouthwash, troche, lozenge, chewing gum, food or drink carrier.

2. A composition according to claim 1 where the active component thereof is 3-n-hexadecyl-4-hydroxymethyl-4-methyloxazolidine.

3. A composition according to claim 1 wherein the active component thereof is 3-n-octadecyl-4-hydroxymethyl-4-methyloxazolidine.

4. A method of treating teeth for preventing the formation of dental plaque thereon which comprises contacting the teeth with an effective amount of a composition according to claim 1.

5. A method according to claim 4 wherein the dental plaque-preventive agent is 3-n-hexadecyl-4-hydroxymethyl-4-methyloxazolidine.

6. A method according to claim 4 wherein the dental plaque-preventive agent is 3-n-octadecyl-4-hydroxymethyl-4-methyloxazolindine.

* * * * *